United States Patent [19]

Shieh

[11] Patent Number: 5,462,646

[45] Date of Patent: Oct. 31, 1995

[54] COATED CAPILLARY COLUMNS AND ELECTROPHORETIC SEPARATION METHODS FOR THEIR USE

[75] Inventor: Chia-Hui Shieh, Irvine, Calif.

[73] Assignee: Beckman Instruments, Inc., Fullerton, Calif.

[21] Appl. No.: 128,914

[22] Filed: Sep. 29, 1993

[51] Int. Cl.⁶ .................. G01N 27/26; G01N 27/447
[52] U.S. Cl. .................... 204/180.1; 204/299 R
[58] Field of Search ................ 204/299 R, 180.8, 204/180.1

[56] References Cited

U.S. PATENT DOCUMENTS 5,181,999  1/1993  Wiktorowicz ................ 204/180.1

OTHER PUBLICATIONS

Tiansong Wang and Richard A. Hartwick, "Capillary modification and evaluation using streaming potential and frontal chromatography for protein analysis in capillary electrophoresis" Journal of Chromatography 594 (1992) 325–334.

Kiyoshi Tsuji & Richard J. Little, "Charged-reversed, polymer-coated capillary column for the analysis of a recombinant chimeric glycoprotein"; Journal of Chromatography, 594 No month available (1992) pp. 317–324.

John E. Wiktorowicz & Joel C. Colburn; "Separation of cationic proteins via charge reversal in capillary electrophoresis"; Electrophoresis 1990 No month available, vol. 11, pp. 769–773.

John K. Towns and Fred E. Regnier; "Polyethyleneimine–bonded phases in the separation of proteins by capillary electrophoresis"; Journal of Chromatography, 516 (1990) No month available pp. 69–78.

Article by Y. J. Yao and S. F. Y. Li; "Capillary Zone Electrophoresis of Basic Proteins with Chitosan as Buffer Additive and as Capillary Coating"; 26 pages no date in article.

Primary Examiner—John Niebling
Assistant Examiner—John S. Starsiak, Jr.
Attorney, Agent, or Firm—William H. May; P. R. Harder; Janis C. Henry

[57] ABSTRACT

Coated capillary electrophoresis columns and methods for their use in electrophoretic separations are disclosed. The coated capillary columns include a length of tubing having an interior surface coated with at least one crosslinked organic multi-valent ionic compound capable of ionic interaction with charged chemical functionalities on the tubing interior surface. Exemplary columns are prepared by crosslinking a multi-functional amine compound with a diexpoxide, alkylating the crosslinked multi-functional amine compound to form a crosslinked quaternary ammonium compound, and then contacting the interior surface of capillary tubing with the crosslinked quaternary ammonium compound.

18 Claims, 3 Drawing Sheets

COATED CAPILLARY COLUMNS AND ELECTROPHORETIC SEPARATION METHODS FOR THEIR USE

BACKGROUND OF THE INVENTION

1. Field of the Invention

The present invention relates generally to capillary columns having interior surface coatings and electrophoretic separation methods for their use. More particularly, the present invention involves capillary columns having a charged crosslinked coating on their interior wall surfaces. The charged coating provides added control over electroosmotic flow, reduces analyte interaction with the interior surface of the capillary column and contributes to the effective electrophoretic separation of amines and related compounds.

2. Description of Relevant Art

Electrophoretic separation techniques have been utilized for years to separate molecules according to differences in the effective charge of the molecules, and/or according to differences in the molecular size of the molecules. Up until recently electrophoretic separations were conducted in gel slabs or open gel beds which were typically fabricated of polyacrylamide gel material. More recently capillary electrophoresis techniques combined with photometric detection methods have allowed the automation and rapid quantitative analysis of molecules. High resolution separations of molecules having different effective charges have been achieved by applying electrophoretic principles to buffer filled or gel filled narrow capillary tubes.

Typically, capillary columns used in capillary electrophoresis are fabricated of lengths of silica tubing having diameters on the order of 25 μm to 200 μm and lengths from about 10 to 200 cm. The buffer and gel separation mediums are pumped directly into the column interiors and electrophoretic techniques are used to separate numerous types of molecules including peptides, proteins, and oligonucleotides, nucleic acids and other charged molecular species. Moreover, the field is continually expanding with respect to the types and sizes of molecules which can be separated and detected using capillary electrophoresis procedures.

The advantages associated with capillary electrophoresis are numerous. Quantitative information can be achieved with very small sample sizes, and the amount of gel or buffer consumed is minuscule. Furthermore, the time required for the separations is sharply reduced, and the technique lends itself to automation and electronic data storage and data manipulation. Significantly, capillary electrophoresis is associated with certain phenomenon which are not present in tradition slab gel electrophoresis. One of these is the now familiar electroosmotic flow phenomenon characterized by bulk flow of buffer solutions toward one of the electrodes.

Electroosmotic flow is generated by the ionization of silanol functionalities on the surface of silica capillary tubing. The ionization results in a layer of protons in the electrophoretic buffer solution at the surface of the silica tubing. In the presence of an electric field the layer of protons resembles a positively charged column of fluid which migrates toward the cathode, causing a general bulk movement of the buffer medium. Advantageously, electroosmotic flow can be utilized in many applications to improve electrophoretic separations. For example, when the electrophoretic migration of the molecules being separated is in the opposite direction to that of electroosmotic flow, the net effect is an increase in effective column length.

Whether or not electroosmotic flow is advantageous for any particular separation, it is desirous to be able to control the flow. One method to minimize or to control electroosmotic flow, is to provide silica capillary tubing coated on the inside with a polymeric material in order to control the degree to which ionization of the surface silanol groups occurs. In general these coatings have served their purpose. However, there is an ongoing need for improved coatings. In particular it is desirous to provide capillary coatings which help control electroosmotic flow and aid in the electrophoretic separations of specific types of sample constituents.

Another problem associated with the capillary electrophoresis is the tendency for sample components to adhere to the wall of the capillary tubing, and in particular silica tubing. This is especially true in the case of small charged molecules which are easily attracted to reactive silica functionalities. When small peptides and amines are present in electrophoretic separation mediums, they interact both electrostatically and hydrophobically with the capillary wall. The result is a decrease in separation efficiency and undesirable band broadening which gives erroneous separation data.

Like electroosmotic flow, providing electrophoresis capillaries which are capable of minimizing or controlling the degree of sample component and wall interaction have not been totally successful. Previous attempts include using a dynamic double layer coating. These bilayer coatings are not stable and require additives in the running buffers used during the electrophoretic process. For separating peptides and proteins, it has been suggested that charged polymeric coatings be applied. However, these column coatings lack physical integrity and coating stability and columns having these coatings having diminished coating life and can have problems with nonreproducible separations. Moreover, small charged molecules by themselves do not have sufficient physical integrity to form effective capillary coatings. Thus, procedures for preparing capillary columns having charged surface coating require utilizing polymers which have a limited availability.

Accordingly, it is an objective of the present invention to provide novel coated capillary columns useful for electrophoresis separations and which provide control over electroosmotic flow.

It is additionally an objective of the present invention to provide capillary columns which reduce or eliminate interactions between sample components and the interior capillary wall.

It is further an objective of the present invention to provide capillaries having physically stable coatings.

It is additionally an objective of the present invention to provide capillaries useful for the electrophoretic separation of a variety of charged molecules.

SUMMARY OF THE INVENTION

The present invention satisfies the above-identified objectives by providing capillary columns having interior surface coatings which contribute to the reduction in the amount of interaction between sample constituents and the interior surface of the capillary column. The coated capillary columns of the present invention additionally contribute to enhancing user control over the degree of electroosmotic flow of bulk material during electrophoretic separations. Advantageously, the coating materials utilized in the capillary columns of the present invention are easily prepared from a variety of readily available organic compounds.

These organic compounds include relatively small molecular weight compounds which preclude the requirement to deal with large polymeric materials. Moreover, use of the capillary columns of the present invention results in improved separations for a number of compounds including amines, peptides, and proteins.

More particularly, the capillary columns of the present invention include a length of tubing with an interior surface having charged chemical functionalities. The interior surface has a coating of crosslinked organic multi-valent ionic compounds capable of ionic interaction with the charged chemical functionalities of the interior surface. In preferred embodiments of the present invention, the tubing is fabricated of silica and the crosslinked organic multi-valent ionic compounds are crosslinked quaternary ammonium compounds.

Exemplary crosslinked quaternary ammonium compounds include those having the general formula:

where $0 \leq n \leq 20$; $0 \leq y \leq 20$ $p \geq 1$;

X is selected from the group consisting of functionalities having the formula Cl, Br, and I;

Z is an organic radical selected from the group consisting of functionalities having the formula:

In preferred embodiments the coated capillary columns of the present invention are prepared by first crosslinking a suitable secondary amine compound, and then alkylating the resulting crosslinked amine compound with a suitable alkylating agent to form the corresponding crosslinked quaternary ammonium compound. Finally, causing the crosslinked quaternary ammonium compound to come in contact with the interior wall of a length of capillary tubing having suitably charged chemical functionalities provides a coated capillary column suitable for use in the electrophoretic separation of charged compounds.

Suitable amine derivatives having utility in the present invention are amine compounds having a least three amino functionalities and capable of being crosslinked with a crosslinking reagent having at least two suitably reactive functionalities. In preferred embodiments the crosslinking reagent is a diepoxide such as butadiene diepoxide. Exemplary, alkylating agents are compounds, such as lower alkyl halides, which are capable of reacting with amine functionalities to form the quaternary ammonium derivative of the amine.

The coated capillary columns of the present invention have particular utility in the electrophoretic separation of analytes having amino and amino derivative functionalities. Exemplary analyte compounds include amines, amino acids, peptides and their derivatives such amine hydrochlorides.

These and other advantages associated with the present invention will become apparent to those skilled in the art upon an understanding the invention as described in the detailed description of the invention taken in combination with the following drawings.

DETAILED DESCRIPTION OF THE INVENTION

The present invention provides coated capillary columns which are particularly useful in electrophoretic separation systems such as the P/ACE series Capillary Electrophoresis Systems manufactured and sold by Beckman Instruments, Inc., Fullerton, Calif. More specifically, the coated capillary columns of the present invention are useful as separation mediums in applications in which a variety of molecular species are separated on the basis of their electrophoretic mobility. These molecular species include macromolecules such as proteins and polynucleotides as well as smaller compounds such as basic drugs and nucleic acids.

The coated capillary columns described herein provide added user control of electroosmotic flow and can be utilized in analytical conditions in which enhanced electroosmotic flow is preferred. As a feature of the present invention, the coating materials used for forming the coated columns are crosslinked compounds or interacting networks of compounds joined by covalent bonds. This results in coatings having enhanced physical integrity which in turn provides columns with longer useful lives and improved reliability and precision in electrophoretic separation procedures. The enhanced physical integrity also contributes to a prolonged ability to prevent the interaction of different analytes with the wall of the capillary column.

Figure 1:
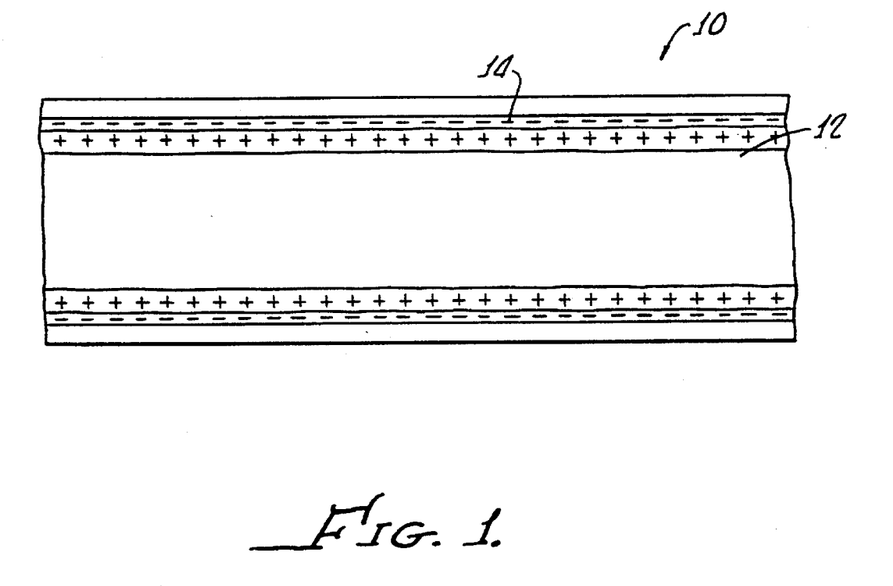
FIG. 1 is a representation of a preferred quaternary ammonium compound ionically interacting with the interior surface of a silica capillary column.

More particularly, and referring to a representative cross-sectional view of a column shown in FIG. 1, the coated capillary columns 10 of the present invention are fabricated of a length of capillary tubing 12 having charged chemical functionalities on its interior surface 14. The interior surface further has a coating of crosslinked organic multi-valent ionic compounds capable of ionic interaction with the charged chemical functionalities of the interior surface.

In preferred embodiments of the present invention, the capillary tubing is fabricated of silica containing glass and the charged chemical moieties are silanol functionalities, $SiO^{-1}$, which are easily formed upon exposing the surface of fused silica to even slightly basic solutions. As known in the art of capillary separation systems, the capillary tubing can vary in length and in diameter, each of which depends upon the particular analytical application. Typically the column will be from between about 10 cm to 200 cm in length and from 25–200 μm in inner diameter.

Suitable organic multi-valent ionic compounds include organic species having an ionic charge opposite that of the charged chemical functionality on the capillary interior surface and having an ionic valency of at least three. Because the crosslinked nature of the coating materials is a feature of the present invention, preferred organic multi-valent ionic compounds are capable of being crosslinked with a crosslinking reagent having at least two functionalities reactive with functionalities present on the multivalent ionic compound.

In accordance with the present invention, and as illustrated in FIG. 1 preferred coated capillary columns are those formed from silica tubing having an interior surface coating of crosslinked quaternary ammonium compounds having the general formula:

where $0 \leq n \leq 20$; $0 \leq y \leq 20$ $p \geq 1$;

X is selected from the group consisting of functionalities having the formula Cl, Br, and I;

Z is an organic radical selected from the group consisting of functionalities having the formula:

$C_1$-$C_{20}$ alkyl, $-C^{=O}-R_1-C^{=O}-$ and $-HCOH-R_2-O-R_3-OHCH-$, where $R_1$, $R_2$, $R_3$ are each independently $C_2$-$C_{20}$ alkyl.

Those skilled in the art will appreciate that once brought into contact with the surface of silica columns as described below, the positive charges on the above-described crosslinked quaternary ammonium compounds will interact with negative charges of the ionized silanol functionalities on the surface of the silica column and ionically bind to the interior surface of the capillary column. It has been determined that crosslinked quaternary ammonium compounds prepared from secondary amine compounds having repeat subunits of as little as three (the value of n in the above formula) are useful coatings for the capillaries of the present invention. There is no limit on upper molecular weight value because the high molecular weight compounds contribute to physical integrity and generally bond easily to the surface of the capillary. Preferred crosslinked quaternary ammonium compounds are preferred from polymeric amine compounds having molecular weights from about 1000 to about 100,000.

The ionic charge density of the crosslinked organic multi-valent ionic compound, which is at least partly determined by the value n, should be sufficiently large to stably and ionically interact with the chemical functionalities on the interior surface of the capillary. Similarly, the ionic charge density should be sufficiently high to mask the charges on the interior surface of the capillary. Thus, the value n can vary substantially, the only limiting criteria being that the multi-valent ionic compound carry sufficient charge to bind to the surface of the capillary column. In preferred embodiments the value n is from about 1 to about 20.

The crosslink density of the crosslinked multi-valent ionic compounds should be sufficiently large to provide a physically stable and mechanically sound coating. Referring to the exemplary coating of FIG. 1, the value n and the amount of crosslinking reagent used in the crosslinking reaction are at least partially determinative of the crosslink density. Amounts of crosslinking reagent which lead to preferred coatings are described in more detail below.

In accordance with the present invention, processes for preparing coated capillary columns include the general steps of providing a length of tubing having an interior surface of charged chemical functionalities and providing a crosslinked organic multi-valent ionic compound capable of ionic interaction with the charged chemical functionalities. Then by causing the organic multi-valent ionic compound to contact the interior surface, a layer of crosslinked multi-valent compound ionically interacts with the interior surface, forming a coated capillary column. As mentioned above, in preferred embodiments the crosslinked organic multi-valent ionic compound is a crosslinked quaternary ammonium compound having the general formula I.

Advantageously, compounds of formula I are prepared by first providing at least one secondary amine compound having the following general formula II, $[-(CH_2)_n-CH_2-NH-(CH_2)_n-CH_2-NH-(CH_2)_n-CH_2-NH-]_p$  II where

$0 \leq n \leq 20$; and $p \geq 1$

Then crosslinking the amine compound, and reacting the crosslinked amine compound with an alkylating reagent to form a crosslinked quaternary ammonium compound. The alkylating reaction can be accomplished in any of a number of volatile organic solvents including lower alkyl alcohols and ethers. Thus, following the alkylating reaction the solution of quaternary ammonium compound and solvent can be caused to contact the crosslinked quaternary ammonium compound with the interior wall of the capillary in order to ionically bond the crosslinked compound with the surface of the interior wall.

Crosslinking multi-functional amine compounds can be accomplished by reacting amine functionalities with a compound having at least two functional moieties capable of reacting with the amine. Because amines readily react with a number of different chemical moieties, a wide variety of multi-functional compounds are available or can be synthesized to act as crosslinking reagents. Because diepoxides readily react with amines in ring opening reactions and because epoxides of varying molecular weight are widely available, diepoxides are preferred for crosslinking multi-functional amines in accordance with the processes of the present invention. As described in more detail below, the most preferred crosslinking reagent is butadiene diepoxide and reacts with the amine shown in II above as follows:

where

0≤n≤20; and p≥1.

Other diepoxides are also suitable including those having the formula:

and wherein R is selected from the group consisting of functionalities having the formula $(CH_2)_n$, $-C\overset{=O}{-}$, and n is an integer between 1 and 20.

While diepoxides, and particularly butadiene diepoxide, are preferred crosslinking reagents, those skilled in the art will appreciate, that other multi-functional compounds can be utilized including a variety of similar diepoxides, dialkyl halides, diacyl halides, and disuccinimides.

Reacting diepoxides with a multi-functional amine compound in order to crosslink the amine compound can be achieved by simply refluxing a solution of amine and diepoxide in a suitable solvent or combination of solvents. The concentration of amine depends upon the solubility and reactivity of the amine. For polymeric amines having molecular weights on the order of 1800, suitable concentrations range from 0.01 wt % to about 50 wt%. Similarly, the concentration of the diepoxide should be high enough to react with a maximum number and amine functionalities and achieve a high crosslink density. Those skilled in the art are credited with varying concentrations and reaction conditions in order to achieve the desired results. The crosslinking reactions between multi-functional amines and diepoxides do not require high temperatures and relatively volatile solvents can be used including ethers and lower alkyl alcohols. These solvents can be easily removed prior to alkylating the crosslinked amine to form the final crosslinked product.

Converting the crosslinked multi-functional amine compound to a crosslinked quaternary ammonium compound is preferably accomplished using any of a number of suitable alkylating agents. While the methods described herein utilize normal alkyl halide alkylating agents, other agents are also suitable. Forming quaternary ammonium compounds from primary, secondary, or tertiary amines using alkyl halides is well-known and those skilled in the art are credited with the knowledge of these reactions. A typical alkylating reaction requires simply combining a selected alkyl halide and the crosslinked amine in a basic solution and refluxing for a suitable length of time. The product of this reaction is a multi-valent ionic compound in the form of a quaternary ammonium salt.

After the alkylating reaction is complete, the resulting solution can be applied directly to the interior surface of a prepared length of capillary tubing. When the capillary tubing is fused silica, the negative silanol functionalities present on the interior surface of silica capillary ionically interact or bind to the positively charged crosslinked quaternary ammonium compounds to form a coating having improved physical integrity and electrophoretic separation characteristics.

The coated capillary columns of the present invention are easily formed and adapted for use in any capillary electrophoresis system. Moreover, their use requires no special handling procedures and typical electrophoretic techniques apply to their use. Accordingly, once positioned in standard capillary electrophoresis equipment, the columns of the present invention can be used in processes for analyzing sample compositions for sample constituents by capillary electrophoresis. In accordance with the present invention, these processes typically include the steps of immersing one end of the coated capillary column in an anodic reservoir and immersing a second end of the coated column in a cathodic reservoir. Then, introducing a sample composition into the interior of the coated column at one end and applying an electric field across the reservoirs will cause the sample constituents to differentially migrate within the capillary column. When a suitable detector, for example a uv-visible detector or fluorescence detector, is appropriately positioned at least one end of the coated column, the separated sample constituents are detected and an electropherogram is generated.

The following examples are offered as being illustrative of exemplary embodiments of the present invention. These examples are non-limiting and are offered as exemplary only.

EXAMPLE 1

The following example illustrates the preparation of a crosslinked polymeric alkyl amine or polyemine (PEI) which has the general formula $$[-CH_2-CH_2-NH-CH_2-CH_2-NH-CH_2-CH_2-NH-]_p$$

A variety of different molecular weights of PEI is available from about 160 to about 1,000,000. The procedure described below is applicable to the preparation of crosslinked PEI 1800, PEI 1200, and PEI 600 as well as a variety of multi-valent amines having similar molecular weight properties.

A 10 g portion of PEI 1800 was add to a solution of 20 mL of methanol and 300 mL of tetrahydrofuran. After the PEI was completely dissolved, a 1.0 g portion of butadiene diepoxide was added to the PEI solution. The resulting solution of PEI and butadiene diepoxide was refluxed for 16 hours then allowed to cool to room temperature. Then 100 mL of water was added to the cooled solution and the methanol and tetrahydrofuran solvents were evaporated from the solution in a rotary evaporator under reduced pressure. The remaining aqueous solution of crosslinked PEI is suitable for use in a subsequent alkylating procedure.

EXAMPLE 2

The following example is illustrative of a procedure for crosslinking low molecular weight multi-valent amines. The described procedure was used interchangeably to crosslink pentaethylenehexamine and triethylenetetramine, having 6 and 4 amine functionalities, respectively.

A 10 gram portion of either pentaethylenehexamine or triethylenetetramine was added to 200 mL of tetrahydrofuran. After the amine was completely dissolved a 1 g portion of butadiene diepoxide was added to the tetrahydrofuran solution and the resulting diepoxide and amine solution was refluxed for 16 hours. The refluxed solution was allowed to cool to room temperature and then 100 mL of water was added to the cooled solution. The tetrahydrofuran portion of the solvent was evaporated on a rotary evaporator under reduced pressure and the resulting aqueous solution of crosslinked amine was suitable for use in an alkylating reaction.

EXAMPLE 3

The following example illustrates a typical method suitable for alkylating crosslinked polymeric amines and smaller crosslinked amine compounds, including the crosslinked PEI's and crosslinked pentaethylenehexamine and triethylenetetramine described above. Although iodomethane is the alkylating reagent utilized in this example, a large number of alkylating agents, including chloro and bromo alkyl compounds are interchangeable with the iodomethane.

A 200 mL volume of methanol, 30 g of sodium carbonate, 100 mL of water, and 50 mL of iodomethane were added to an aqueous solution containing 10 grams multi-valent amine compound crosslinked as described in EXAMPLE 1 or EXAMPLE 2. The reaction mixture was allowed to reflux for 16 hours and the methanol was removed using a rotary evaporator under reduced pressure. The resulting quaternary ammonium compound aqueous solution was diluted to 1000 mL total volume and then filtered through of 0.45 µm pore size filter. This filtered solution is suitable for applying to the interior surface of capillary tubing in order to form an ionically interacting coating.

EXAMPLE 4

The following example is exemplary of methods suitable for preparing capillary tubing and methods for forming the coating on the interior surface of the tubing in order to provide the final coated capillary column.

The interior surfaces of a length of 50 µm diameter capillary tubing purchased from Polymicro of Phoenix, Ariz. was rinsed with a solution of 1N HCl for 15 minutes. The HCl solution was removed and the interior of the tubing was rinsed with a 1N solution of NaOH for 15 minutes which was followed by a clear water rinse for 15 minutes. Then the prepared length of capillary column was rinsed for 15 minutes with an aqueous solution containing about 1% by weight of crosslinked quaternary ammonium compound. Following this rinsing step the coated capillary column was suitable for use in standard capillary electrophoresis procedures.

EXAMPLE 5

The following illustrates exemplary applications for the coated capillary columns of the present invention. In particular, as described below and shown in FIG. 2., the coated columns of the present invention are useful in the separation of small charged particles such as basic drugs and larger proteins.

Figure 2:
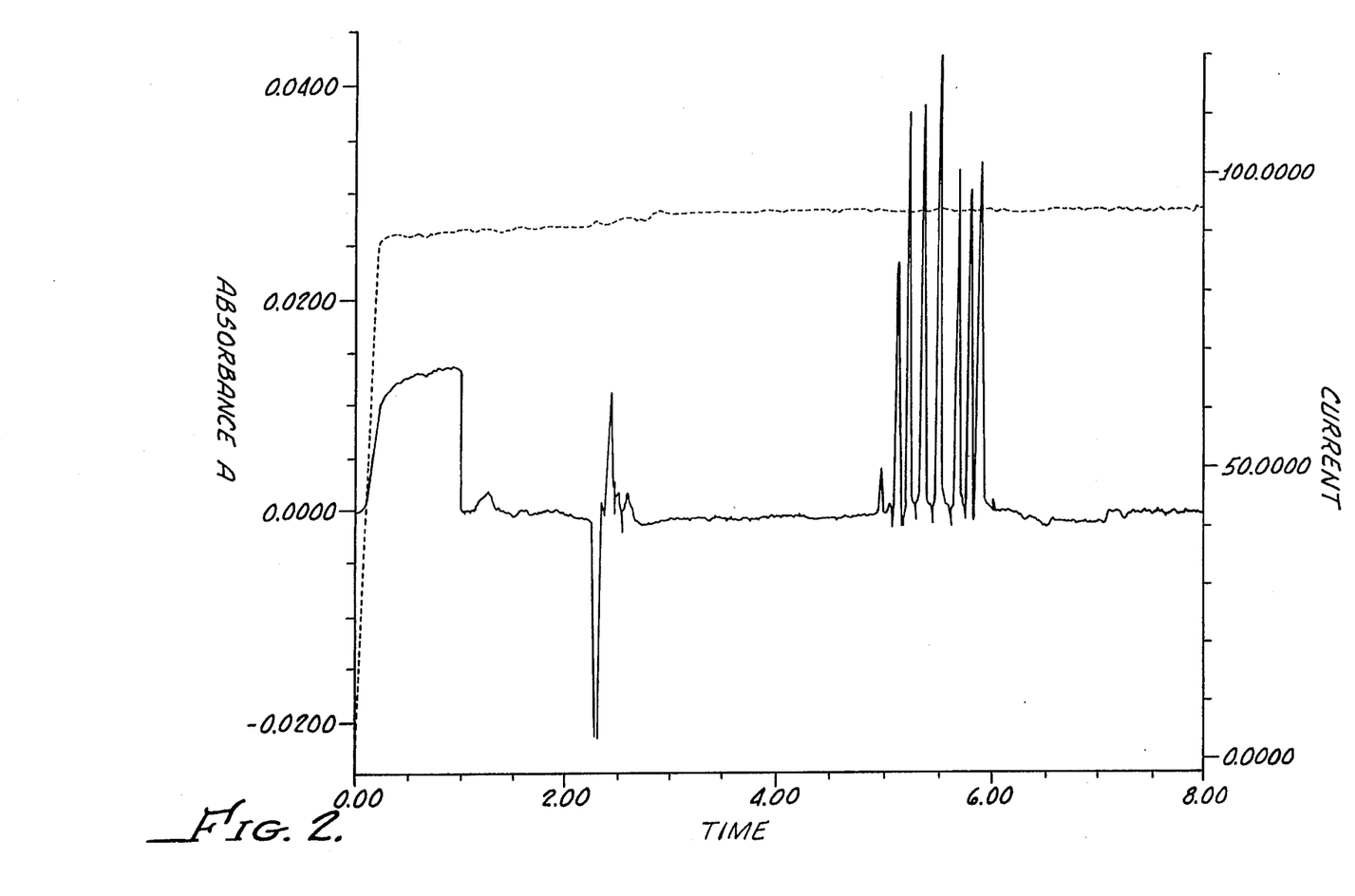
FIG. 2 is an electropherogram resulting from the electrophoretic separation of seven basic drugs in an aqueous solution in accordance with the present invention.

An aqueous sample containing 7 basic drugs was prepared by adding 1.0 mg each of Desipramine, Imipramine, Nordoxepin, Doxepin, Nortriptyline, Amitriptyline, and Protriptyline to 1.0 mL of water. A 37 cm×50 µm capillary column coated with crosslinked and alkylated PEI 1800 (crosslinked and alklyated as described in EXAMPLE 1 and EXAMPLE 2) was positioned in a P/ACE capillary electrophoresis instrument (manufactured by Beckman Instruments, Inc., Fullerton, Calif.). The column was filled with a buffer of 50 mM bistris propane adjusted to a pH of 6.5. The sample of the basic drug solution was injected into one end of the column using a 10 sec pressure injection and 400 V/cm or 14.8 kV was applied across the electrophoresis reservoirs at a temperature of 25° C. The separated basic amines were detected with a uv detector at 214 run. FIG. 2 shows the electropherogram which was obtained after less than 8 minutes of migration. Each of the basic amines was separated from the other amines by a baseline separation. The order of migration, from left to right on the electropherogram is Doxepin, Nordoxepin, Imipramine, Desipramine, Amitriptyline, Nortriptyline, and Protriptyline.

EXAMPLE 6

The following illustrates an exemplary application for the coated capillary columns of the present invention. In particular, as described below and shown in FIG. 3, the coated columns of the present invention are useful in the separation of proteins.

Figure 3:
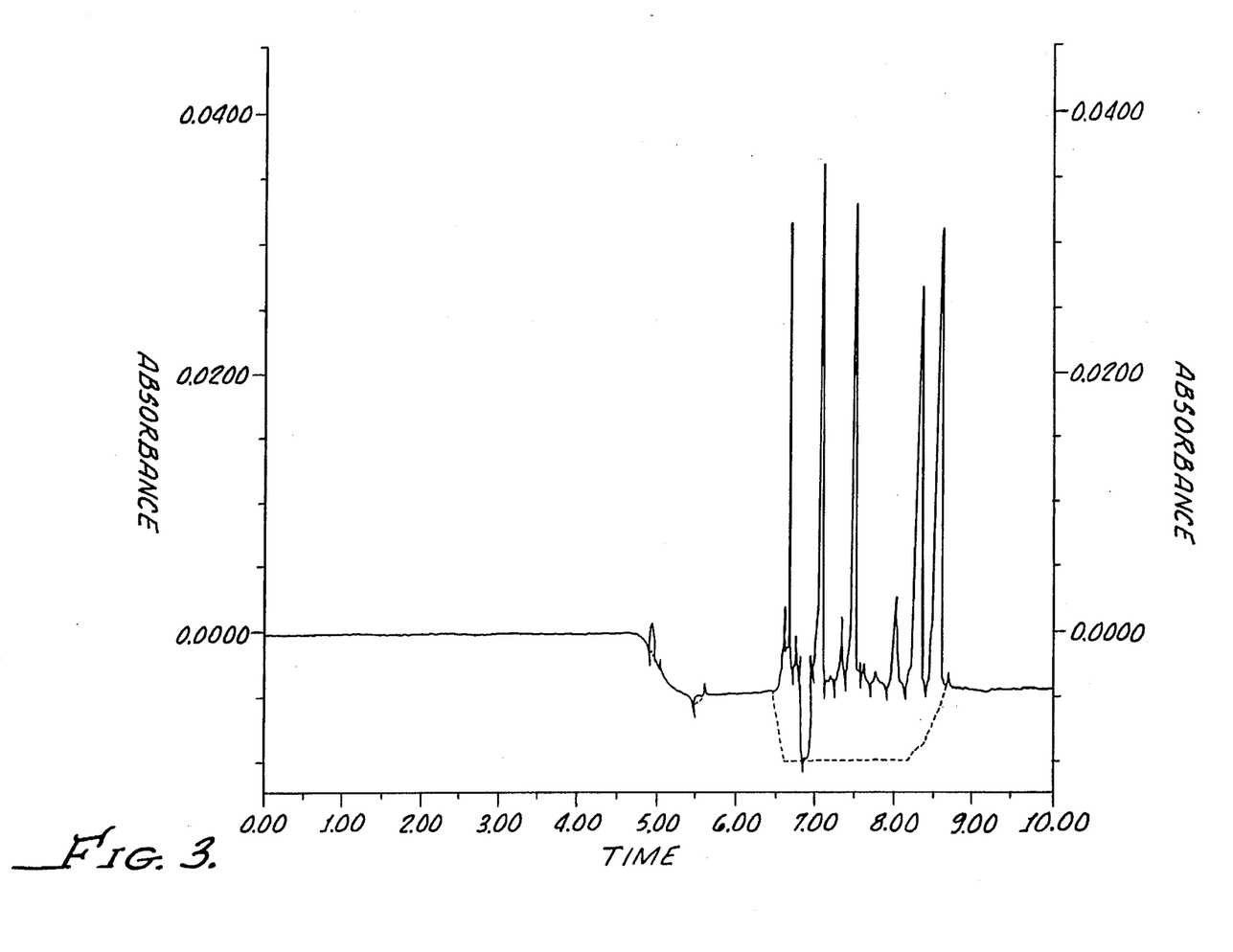
FIG. 3 is an electropherogram resulting from the electrophoretic separation of proteins in an aqueous solution in accordance with the present invention.

An aqueous sample containing 5 proteins was prepared by adding 1.0 mg each of carbonic anhydrase, myoglobin, α-chymotrypsinogen A, cytochrome C, and lysozyme to 1.0 mL of water. A 37 cm×50 µm capillary column coated with crosslinked and alkylated PEI 1800 (crosslinked and alklyated as described in EXAMPLE 1 and EXAMPLE 2) was positioned in a P/ACE capillary electrophoresis instrument (manufactured by Beckman Instruments, Inc., Fullerton, Calif.). The column was filled with a HEPES buffer adjusted to a pH of 7.0. The sample of the basic drug solution was injected into one end of the column using a 10 sec pressure injection and 300 V/cm or 11.1 kV was applied across the electrophoresis reservoirs at a temperature of 25° C. The separated basic proteins were detected with a uv detector at 214 nm. FIG. 3 shows the electropherogram which was obtained after less than 8 minutes of migration. Each of the proteins was separated from the other proteins by a baseline separation with the migration order left to right on the electropherogram being carbonic anhydrase, myoglobin, α-chymotrypsinogen A, cycochrome C, and lysozyme.

What is claimed is:

1. A capillary column for electrophoretic separations of sample components, said capillary column comprising:
   a length of tubing having an interior surface, said interior surface having charged chemical functionalities; and
   a coating on said interior surface, said coating comprising at least one crosslinked organic quaternary ammonium compound capable of ionic interaction with said charged chemical functionalities of said interior surface.

2. The capillary column of claim 1 wherein said tubing is fabricated of silica and said charged chemical functionalities include ionized silanol functionalities.

3. The capillary column of claim 1 wherein said quaternary ammonium compounds includes compounds having a least three quaternary ammonium functionalities.

4. The capillary column of claim 1 wherein said crosslinked quaternary ammonium compound is selected from the group consisting of compounds having the formula:

where $0 \leq n \leq 20$; $0 \leq y \leq 20$;

$p \geq 1$;

X is selected from the group consisting of functionalities having the formula Cl, Br, and I;

Z is an organic radical selected from the group consisting of functionalities having the formula:

$C_1-C_{20}$ alkyl, $-C^{=O}-R_1-C^{=O}-$, and $-$HCOH$-$ $R_2-O-R_3-$HOCH, where $R_1$, $R_2$, $R_3$ are each independently $C_1-C_{20}$ alkyl.

5. A capillary column for electrophoretic separations of sample components, said capillary column comprising:

a length of silica tubing having an interior surface, said interior surface having charged dissociated silanol functionalities; and a coating on said interior surface, said coating comprising crosslinked quaternary ammonium compounds capable of ionic interaction with said dissociated silanol functionalities.

6. The capillary column of claim 5 wherein said crosslinked quaternary ammonium compounds include compounds having a least three quaternary ammonium functionalities crosslinked with a diepoxide compound.

7. The capillary column of claim 6 wherein said crosslinked quaternary ammonium compound is selected from the group consisting of compounds having the formula:

where $0 \leq n \leq 20$; $0 \leq y \leq 20$;

$p \geq 1$;

X is selected from the group consisting of functionalities having the formula Cl, Br, and I;

Z is an organic radical selected from the group consisting of functionalities having the formula:

$C_1-C_{20}$ alkyl, $-C^{=O}-R_1-C^{=O}-$, and $-$OHCH$-$ $R_2-O-R_3-$OHCH, where $R_1$, $R_2$, $R_3$ are each independently $C_1-C_{20}$ alkyl.

8. A process for preparing a capillary column, said process comprising the steps:

providing a length of tubing having an interior surface, said interior surface having charged chemical functionalities;

providing a crosslinked organic multi-valent ionic compound, said crosslinked multi-valent ionic compound being capable of ionic interaction with said charged chemical functionalities;

causing said crosslinked multi-valent ionic compound to contact said interior surface, thereby forming a layer of crosslinked multi-valent compound ionically interacting with said interior surface.

9. The process of claim 8 wherein providing a crosslinked multi-valent ionic compound comprises providing a crosslinked quaternary ammonium compound.

10. The process of claim 9 wherein providing a crosslinked quaternary ammonium compound is accomplished by providing at least one amine compound, said amine having at least three amine functionalities per molecule;

crosslinking said amine compound to provide a crosslinked amine compound; and reacting said crosslinked amine compound with an alkylating agent to form a crosslinked quaternary ammonium compound.

11. The process of claim 10 wherein said amine compound is selected from the group of amines having the formula where $0 \leq n \leq 20$;

$p \geq 1$.

12. The process of claim 10 wherein crosslinking said amine compound is accomplished by reacting amine functionalities of said amine with a crosslinking reagent selected from the group consisting of diepoxides, dialkyl halides, diacyl halides, and disuccinimides.

13. The process of claim 12 wherein said diepoxide is selected from the group consisting of compounds having the formula:

and wherein R is selected from the group consisting of functionalities having the formula $(CH_2)_n$, $-C^{=O}-$, and n is an integer between 1 and 20.

14. The process of claim 10 wherein said crosslinked quaternary ammonium compound is selected from the group consisting of compounds having the formula:

where $0 \leq n \leq 20$; $0 \leq y \leq 20$;

$p \geq 1$;

X is selected from the group consisting of functionalities having the formula Cl, Br, and I;

Z is an organic radical selected from the group consisting of functionalities having the formula:
$C_1$–$C_{20}$ alkyl, —$C^{=O}$—$R_1$—$C^{=O}$—, and —HCOH—$R_2$—O—$R_3$—HOCH, where $R_1$, $R_2$, $R_3$ are each independently $C_1$–$C_{20}$ alkyl.

15. The process of claim 10 wherein reacting said crosslinked amine compound with an alkylating agent to form a crosslinked quaternary ammonium compound is accomplished by reacting said crosslinked amine compound with an alkyl halide alkylating agent.

16. A process for analyzing a sample composition for sample constituents by capillary electrophoresis, said process comprising the steps:

providing a capillary electrophoresis column comprising:

a length of capillary tubing having an interior surface, a first end, and a second end said interior surface having charged chemical functionalities; and a coating on said interior surface, said coating comprising crosslinked organic quaternary ammonium compounds capable of ionic interaction with said charged chemical functionalities of said interior surface;

immersing said first end in an anodic reservoir and immersing said second end in a cathodic reservoir;

introducing said sample composition into said length of capillary tubing at said first end or said second end; and applying an electric field across said reservoirs, said electric field capable of causing said sample constituents to migrate at different rates with respect to each sample constituent within said capillary column.

17. The process of claim 16 wherein said sample constituents are selected from the group consisting of peptides, proteins, and amines.

18. The process of claim 16 wherein said crosslinked organic quaternary ammonium compound is selected from the group consisting of compounds having the formula:

where $0 \leq n \leq 20$; $0 \leq y \leq 20$;

$p \geq 1$;

X is selected from the group consisting of functionalities having the formula Cl, Br, and I;

Z is an organic radical selected from the group consisting of functionalities having the formula:
$C_1$–$C_{20}$ alkyl, —$C^{=O}$—$R_1$—$C^{=O}$—, and —HCOH—$R_2$—0—$R_3$—HOCH, where $R_1$, $R_2$, $R_3$ are each independently $C_1$–$C_{20}$ alkyl.

* * * * *